United States Patent [19]
Vedamuthu et al.

[11] Patent Number: 5,231,165
[45] Date of Patent: Jul. 27, 1993

[54] BACTERIOCIN FROM LACTOCOCCUS LACTIS SUBSPECIES LACTIS

[75] Inventors: Ebenezer R. Vedamuthu; James T. Henderson, both of Bradenton, Fla.; John D. Marugg, Utrecht; Pieter D. VanWassenaar, Maassluis, both of Netherlands

[73] Assignee: Quest International Flavors and Food Ingredients Co., division of Indopco, Inc., Bridgewater, N.J.

[21] Appl. No.: 882,715

[22] Filed: May 14, 1992

Related U.S. Application Data

[62] Division of Ser. No. 721,774, Jul. 1, 1991, Pat. No. 5,173,297.

[51] Int. Cl.⁵ .................................................. C07K 7/10
[52] U.S. Cl. ............................... 530/324; 435/68.1; 435/71.3; 435/885; 530/349; 426/9; 426/34; 426/326; 424/418
[58] Field of Search ................ 424/115, 418; 530/324; 514/2; 435/88.5, 71.3, 68.1; 426/9, 34, 326

[56] References Cited

U.S. PATENT DOCUMENTS

| | | | |
|---|---|---|---|
| 4,716,115 | 12/1987 | Gonzalez et al. | 435/172.3 |
| 4,740,593 | 4/1988 | Gonzalez | 435/243 |
| 4,883,673 | 11/1989 | Gonzalez | 424/195.1 |
| 4,929,445 | 5/1990 | Vandenbergh et al. | 424/115 |

OTHER PUBLICATIONS

Klaenhammer, Biochimie 70:337–349 (1988).
Klaenhammer, T. R., Biochimie. 70:337–349 (1988).
Hurst, A., Advances Appl. Microbiol. 27:85–123 (1981).
Foster, E. M., F. E. Nelson, M. L. Speck, R. N. Doetsch, and J. C. Olson, Jr., Dairy Microbiology Prentice-Hall Inc, Englewood Cliffs, N.J. p. 15 (1957).
Delves-Broughton, J. Food Technology, 44:100–112, 117 (1990).
Geis, A., Kieler Milchwirtschaftliche Forschungsberichte 41:97–104 (1989).
Buchman, G. W., et al., J. Biol. Chem. 263:16260–16266 (1988).
Kaletta, C. and K-D Entian., J. Bacteriol. 171:1597–1601 (1989).
Chan, W. C., et al., FEBS Lett. 252:29–36 (1989).
Barber, M., et al., Experentia 44:266–270 (1988).
Slijper, M., et al., FEBS Lett. 252:22–28 (1989).
Liu, W. and J. N. Hansen, Appl. Environ. Microbiol. 56:2551–2558 (1990).
Schnell, N., et al., Nature 333:276–278 (1988).
Weil, H-P., et al., Eur. J. Biochem. 194:217–223 (1990).
Wakamiya, T., et al., Tet. Lett. 29:4771–4772 (1988).
Kellner, R. and G. Jung., Proc. 20th Europ. Peptide Sym. 366–368 (1988).
Speck, M. L., Compendium of Methods for the Microbiological Examination of Foods, America Public Health Association, Washington, D.C., pp. 184–194 (1984).
Gonzalez, C. F., and B. S. Kunka, Appl. Environ. Microbiol. 53:2534–2538 (1987).
Gonzalez, C. F. and B. S. Kunka, Appl. Environ. Microbiol. 46:81–89 (1983).
Deutcher, M. P., Meth. Enzymol. 182:611–612 (1990).
Bhunia, J. Ind. Micro. Biol. 2:319–322 (1987).
Van der Vossen, J. M. D., van der Lelie, D., and Venema, G., Appl. Environ. Mic. 53:2452–2457 (1987).
Dodd, H. M., Horn, N., and Gasson, M. J., J. Gen. Microbiol. 136:555–566 (1990).
Barone, A. D., et al., Nucleic Acid Research, 12:4051–4061 (1984).
Maniatis, T., Fritsch, E. F., and Sambrook, J., Molecular Cloning: A Laboratory Manual. Cold Spring Harbor, N.Y. (1982).
Sanger, F., Nicklen, S., and Coulson, A. R., Proc. Natl. Acad. Sci. USA 74:5463–5467 (1977).
Biggin, M. D., et al., Proc. Natl. Acad. Sci. USA 80:3963–3965 (1983).

*Primary Examiner*—Robert A. Wax
*Assistant Examiner*—David B. Schnickel
*Attorney, Agent, or Firm*—Ian C. McLeod

[57] ABSTRACT

A bacteriocin or polypeptide (LL-2 SEQ ID NO:2) derived from *Lactococcus lactis* subspecies lactis NRRL-B-18809 is described. Sequenced DNA and polypeptide precursor encoded thereby (SEQ ID NO: 1) are described Methods of use and production of the polypeptide LL-2 are described.

9 Claims, 3 Drawing Sheets

1-47000, 2-33000, 3-24000,
4-16000 DALTONS

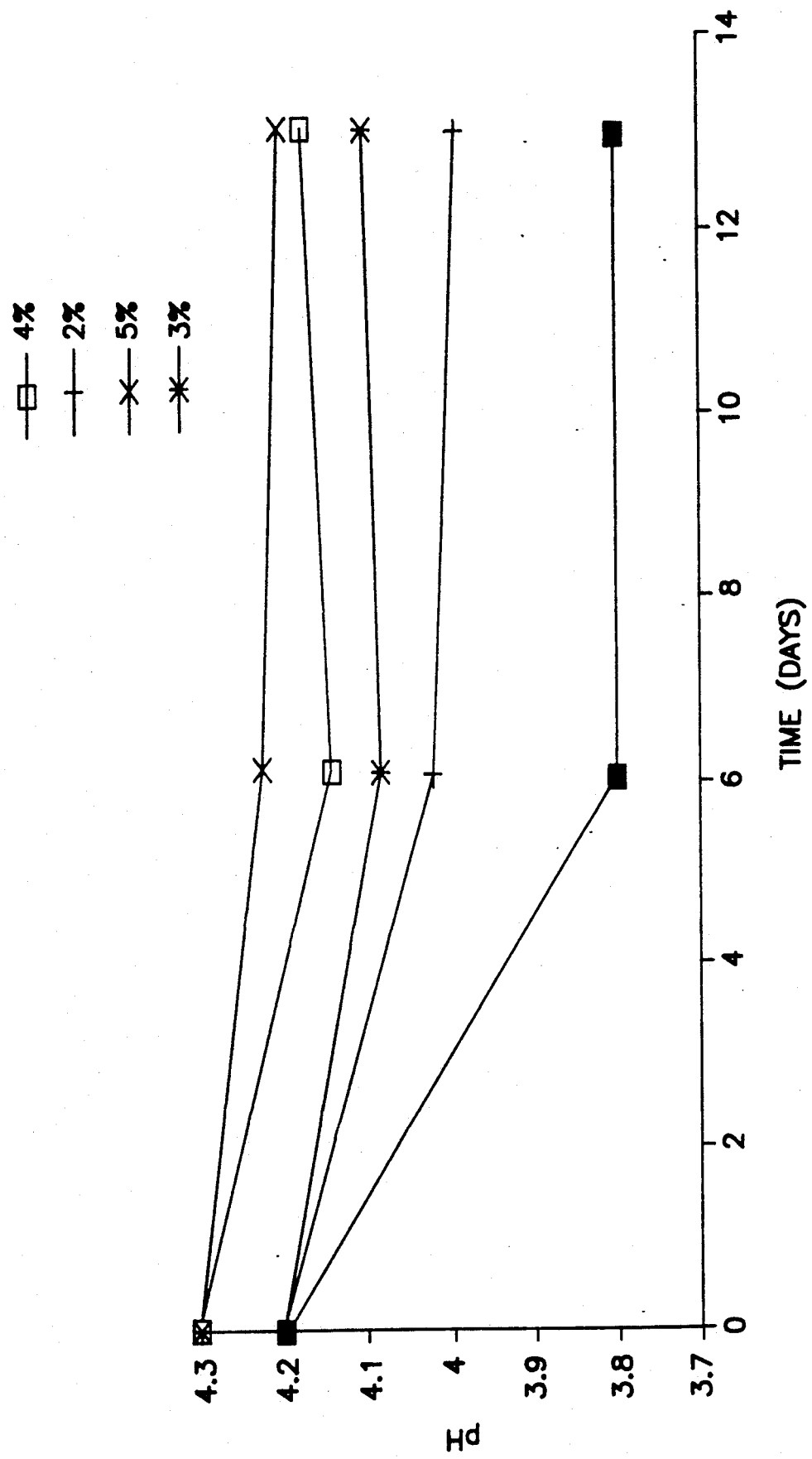

BACTERIOCIN FROM LACTOCOCCUS LACTIS SUBSPECIES LACTIS

This is a divisional of copending application Ser. No. 07/721,774 filed on Jul. 1, 1991 now U.S. Pat. No. 5,173,277.

BACKGROUND OF THE INVENTION

(1) Field of the Invention

The present invention relates to a novel polypeptide, also referred to as a bacteriocin, produced by *Lactococcus lactis* subspecies lactis which is inhibitory against selected Gram-positive bacteria, to a method of inhibiting the Gram-positive bacteria with the bacteriocin and to methods for producing the bacteriocin. In particular, the present invention relates to a bacteriocin encoded by DNA from *Lactococcus lactis* subspecies lactis NRRL-B-18809 and to a precursor polypeptide which is post translationally modified after expression of the DNA.

(2) Prior Art

Lactic acid bacteria comprise a group of Gram-positive spherical and rod-shaped bacteria that are usually non-pathogenic and fermentative. The genera included in this group are Lactococcus, Streptococcus, Lactobacillus and Pediococcus. Many members of these genera are traditionally used in food fermentations and are considered "generally regarded as safe" (GRAS). Production of antagonistic substances and bacteriocins by lactic acid bacteria has been widely reported (Klaenhammer, T. R., Biochimie. 70:337-349 (1988)). Some of the bacteriocins elaborated by these bacteria have a rather narrow spectrum (for example, closely related species) while others exhibit a broader spectrum crossing even the genus grouping. Members of the genus Lactococcus commonly used as starter cultures in fermented foods are *Lactococcus lactis* subsp. lactis, and *Lactococcus lactis* subsp. cremoris. Both these species produce bacteriocins. A well characterized and nomenclaturally recognized bacteriocin from *Lactococcus lactis* subsp. lactis is nisin. *Lactococcus lactis* subsp. cremoris produces diplococcin. Nisin has a wide antibacterial spectrum (Hurst, A., Advances Appl. Microbiol. 27:85-123 (1981)) while diplococcin is primarily active against *Lactococcus lactis* subsp. lactis and other non-bacteriocin producing *Lactococcus lactis* subsp. cremoris strains (Foster, E. M., F. E. Nelson, M. L. Speck, R. N. Doetsch, and J. C. Olson, Jr., Dairy Microbiology, Prentice-Hall Inc., Englewood Cliffs, N.J. p.15 (1957)). Because of the wide antibacterial activity of nisin and its potential applications (Hurst, A., Advances Appl. Microbiol. 27:85-123 (1981); Delves-Broughton, J. Food Technology, 44:100-112, 117 (1990)), a search for other strains within this group that elaborate different bacteriocin(s) with wide antibacterial spectra was made.

Structural characteristics of nisin are well documented in several review articles (Klaenhammer, T. R., Biochimie, 70:337-349 (1988); Geis, A., Kieler Milchwirtschaftliche Forschungsberichte 41:97-104 (1989)). The nucleotide sequence of the nisin gene is known (Buchman, G. W., et al., J. Biol. Chem. 263:16260-16266 (1988)) and descriptions of its post-translational modifications (Kaletta, C. and K-D Entian., J. Bacteriol. 171:1597-1601 (1989)) and degradation products (Chan, W. C., et al., FEBS Lett. 252:29-36 (1989); Barber, M., et al., Experentia 44:266-270 (1988)) have appeared. The solution conformation of nisin was determined (Slijper, M., et al., FEBS Lett. 252:22-28 (1989)) as well as other physical and chemical properties (Liu, W. and J. N. Hansen, Appl. Environ. Microbiol. 56:2551-2558 (1990)).

Nisin is similar to other known lanthionine containing bacteriocins, including epidermin (Schnell, N., et al., Nature 333:276-278 (1988)) pep 5 (Weil, H-P., et al., Eur. J. Biochem. 194:217-223 (1990)), lanthiopeptin (Wakamiya, T., et al., Tet. Lett. 29:4771-4772 (1988)), ancovenin (Wakamiya, T., et al., Tet. Lett. 29:4771-4772 (1988)), subtilin (Buchman, G. W., et al., J. Biol. Chem. 263:16260-16266 (1988)), and gallidermin (Kellner, R. and G. Jung., Proc. 20th Europ. Peptide Sym. 366-368 (1988)). The aforementioned lantibiotics share characteristics of small (3500 Da), basic (pI > 10) post-translationally modified proteins with an inhibitory spectrum limited to gram positive bacteria. Nisin has been attributed the ability to limit sporulation of Bacilli and Clostridia.

U.S. Pat. No. 4,883,673 to Gonzalez describes a pediocin. U.S. Pat. No. 4,929,445 to Vandenbergh et al describes the DNA encoding the pediocin. U.S. Pat. Nos. 4,740,593 and 4,716,115 to Gonzalez et al describe microorganisms containing DNA from a nisin producing microorganism transferred to a non-nisin producing microorganism using various techniques for manipulating the DNA. The prior art also describes the production of antifungal substances from Lactococcus and Pediococcus which are unrelated to the present invention.

U.S. patent application Ser. No. 07/492,969 assigned to a common assignee describes bacteriocin LL-1 from *Lactococcus lactis* NRRL-B-18535. This strain produces a bacteriocin which is related to nisin whereas the bacteriocin LL-2 of the present invention is different from nisin.

OBJECTS

It is therefore an object of the present invention to provide a novel bacteriocin derived from DNA of *Lactococcus lactis* subspecies lactis NRRL-B-18809. Further, it is an object of the present invention to provide the DNA encoding a precursor polypeptide to the bacteriocin. Further still, it is an object of the present invention to provide a method for inhibiting selected Gram-positive bacteria using the bacteriocin. Finally, it is an object of the present invention to provide a method for producing the bacteriocin. These and other objects will become increasingly apparent by reference to the following description and the drawings.

IN THE DRAWINGS

FIG. 3 is a graph showing the effects of various percentages of crude bacteriocin in yogurt.

GENERAL DESCRIPTION

Figure 1A:
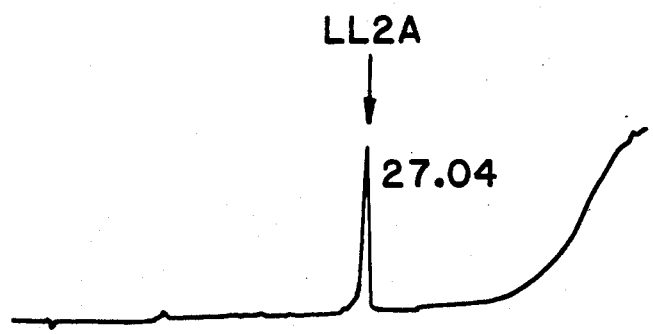
FIGS. 1A and 1B show high performance liquid chromatography (HPLC) chromatographs of the LL-2A, LL-2B and nisin. They show that LL-2A and LL-2B are different from nisin.

The present invention relates to a polypeptide having an inhibitory activity against sensitive Gram-positive bacteria and having the amino acid sequence Ile Xab Xaa Ile Xaa Leu Xac Xab Pro Gly Xac Lys Xab Gly Ala
1               5                   10              15

Leu Met Gly Xac Asn Met Lys Xab Ala Xab Xac Asn Xac Xaa Ile
        20              25              30

His Val Xaa Lys wherein Xaa is selected from Ser, Ala-, or Dha, and Xab is selected from Abu-, or Dhb, and Xac is selected from Ala-S-, where Ala- is 3-substituted Alanine (—(-CO)CH(NH—)CH$_2$—), Abu- is 3 substituted 2-aminobutanoic acid (—(CO)CH(NH—)CH(CH$_3$)—), Ala-S- is (3-alanyl)-thio, Abu is 2-amino butanoic acid, Dha is 2-amino propenoic acid and Dhb is 2-aminobut-2-enoic acid, and subunits thereof having an essentially equivalent inhibitory activity to the sensitive bacteria.

The present invention particularly relates to a polypeptide produced by *Lactococcus lactis* subspecies lactis NRRL-B-18809 in a growth medium and having inhibitory activity against sensitive Gram-positive bacteria.

The present invention further relates to a method for producing DNA comprising the gene encoding a precursor polypeptide of a polypeptide, the latter polypeptide having inhibiting activity against selected Gram-positive bacteria, which method comprises: providing DNA obtained from *Lactococcus lactis* subspecies lactis NRRL-B-18809 comprising a DNA sequence encoding a precursor polypeptide of the polypeptide described above; and subjecting the DNA to a polymerase chain reaction wherein the primers are: 5'-CGCGAG-CATAATAAACGGCT-3' as a sense primer and 5'-GGATAGTATCCATGTCTGAAC-3' as an antisense primer to produce a DNA sequence comprising the gene encoding said precursor polypeptide.

The present invention particularly relates to the DNA sequence encoding a precursor polypeptide, said DNA sequence being the polynucleotide 1-321 tive Gram-positive bacteria which comprises: providing a lactic acid bacterium containing DNA as carried in *Lactococcus lactis* subspecies lactis NRRL-B-18809 in a growth medium containing a carbon source, a nitrogen source and minerals under conditions to express the polypeptide having the inhibitory activity against the selected bacteria; and optionally isolating the polypeptide from the growth medium. In particular the present invention relates to a process for purifying a polypeptide produced by a culture of *Lactococcus lactis* subspecies lactis NRRL-B-18809, in which the purification is performed by passing a broth fermented by the culture through a chromatography column, preferably using an anion exchange resin, and the polypeptide containing product in purified form is collected from the chromatography column, preferably by controlled elution from the column.

The present invention further relates to a method wherein the polypeptide is used to inhibit sensitive Gram-positive bacteria. In particular the present invention relates to a method for inhibiting sensitive Gram-positive bacteria which comprises: exposing the bacteria to an inhibitory amount of the polypeptide described previously to thereby inhibit the bacteria.

*Lactococcus lactis* subspecies lactis NRRL-B-18809 is deposited under the Budapest Treaty with the Northern Regional Research Laboratory in Peoria, Ill. and is available upon request by name and accession number. Plasmid pSRQ 400 which encodes for the bateriocin LL-2 is carried by this deposit. The strain has the following salient fermentation characteristics: sucrose-positive, lactose-positive, milk coagulated, and arginine deaminase positive.

The plasmid pSRQ 400 can be transferred to other Lactococcus species by mating or by various known techniques for transferring plasmids between microorganisms. The DNA encoding a precursor polypeptide to the bacteriocin can also be transferred to various

| | |
|---|---|
| CGCGAGCATA ATAAACGGCT CTGATTAAAT TCTGAAGTTT GTTAGATACA ATGATTTCGT | 60 |
| TCGAAGGAAC TACAAAATAA ATTATAAGGA GGCACTCAAA ATG AGT ACA AAA GAT | 115 |
| TTT AAC TTG GAT TTG GTA TCT GTT TCG AAG AAA GAT TCA GGT GCA TCA | 163 |
| CCA CGC ATT ACA AGT ATT TCG CTA TGT ACA CCC GGT TGT AAA ACA GGA | 211 |
| GCT CTG ATG GGT TGT AAC ATG AAA ACA GCA ACT TGT AAT TGT AGT ATT | 259 |
| CAG GTA AGC AAA TAACC AAATCAAAGG ATAGTATTTT GTTAGTTCAG ACATGGATAC | 316 |
| TATCC | 321 |

Further the present invention relates to a precursor polypeptide having the sequence Met Ser Thr Lys Asp
        −20

Phe Asn Leu Asp Leu Val Ser Val Ser Lys Lys Asp Ser Gly Ala Ser
        −15              −10                 −5

Pro Arg Ile Thr Ser Ile Ser Leu Cys Thr Pro Gly Cys Lys Thr Gly
1               5                       10

Ala Leu Met Gly Cys Asn Met Lys Thr Ala Thr Cys Asn Cys Ser Ile
15              20              25              30

His Val Ser Lys
        34

The present invention also relates to a method for producing a polypeptide having activity against sensimicroorganisms using recombinant genetic techniques with vectors as is well known to those skilled in the art.

When the bacteriocin is produced in culture, it is preferably isolated and purified. The bacteriocin aggregates to about 100,000 daltons and thus can be initially purified by ultrafiltration where the bacteriocin is the retentate. The bacteriocin can then be purified by HPLC.

The bacteriocin is used to inhibit selected Gram-positive bacteria including:
Lactobacillus plantarum;
Lactobacillus casei;
Lactobacillus brevis;
Lactobacillus bulgaricus;
Lactobacillus fermentum;
Pediococcus acidilactici;
Pediococcus pentosaceus;
Streptococcus mutans;
Bacillus subtilis; and
Lactococcus lactis.

The crude LL-2 is not as effective as the bacteriocin purified by HLC which is to be expected since the purified bacteriocin has a higher activity per unit volume. The LL-2 is separable into LL-2A and LL-2B. The former polypeptide is derived from the latter.

The activity of the bacteriocin is expressed in Arbitrary Units (AU) per ml. The AU is defined as five (5) microliters of the highest dilution of culture supernatant yielding a definite zone of growth inhibition against the indicator strain which in this case is *Pediococcus pentosaceus* FBB63C. The titer is expressed as the reciprocal of the highest dilution showing inhibition.

The culture supernatant contains about 1600 AU per ml of the bacteriocin. The HPLC purified bacteriocin exhibited about 2,500,000 AU per ml. In general, between about 15 and 100 AU per gram of a material being treated is sufficient to provide inhibition.

The materials being treated to provide inhibition are preferably foods. Other non-food materials can also be treated with the bacteriocin.

SPECIFIC DESCRIPTION

Example 1

This Example shows the isolation and characterization of *Lactococcus lactis* subspecies lactis NRRL-B-18809 and the bacteriocin produced therefrom.

Isolation of lactic acid bacteria. To obtain a wide selection of naturally occurring "wild" strains of lactic acid bacteria, samples of natural habitats of these bacteria such as raw milk, fermenting vegetable matter and fruits, and fresh vegetables were plated on suitable media with or without enrichment (Speck, M. L., Compendium of Methods for the Microbiological Examination of Foods, American Public Health Association, Washington, D. C., pp. 184–194 (1984)). Enrichment generally involved using high concentrations of common salt (NaCl)—from 2%–6% in broth cultures followed by plating on solid media containing the same levels of NaCl.

Screening for antimicrobial activity. Colonies appearing on the agar plates were screened for antibacterial activity against a selected indicator, which usually predicted a wide antibacterial spectrum. The indicator chosen was *Pediococcus pentosaceus* FBB63C (Gonzalez, C. F., and B. S. Kunka, Appl. Environ. Microbiol. 53:2534–2538 (1987) and U.S. Pat. No. 4,883,673 to Gonzalez. Antibacterial activity was determined by picking colonies to replicate agar plates containing 1.9% sodium beta-glycerophosphate as buffer and after appearance of colonies overlaying with indicator.

Characterization of antimicrobial isolates. Cultures showing antibacterial activity were examined for Gram-staining reactions, cell morphology and arrangement, key carbohydrate fermentations using purple base broth with specific carbohydrate, and for ability to coagulate milk.

Bacteriocin assay. To ascertain if the antibacterial substance is secreted into liquid medium, the cultures were grown in MRS broth and cell free filtrates of turbid cultures were made and the filtrate posted on a seeded semisolid agar overlay of the indicator. Antibacterial activity was quantitated by assigning arbitrary units. One arbitrary unit (AU) was defined as 5 $\mu$l of the culture supernatant yielding a definite, clear zone of inhibition on the indicator lawn. The titer was expressed as the reciprocal of the highest dilution of supernatant showing inhibition.

Preliminary characterization of crude bacteriocin. Preliminary characterization of the bacteriocins with respect to size, molecular weight, pH optimum, effect of enzymes, and effect of nutritive supplements on bacteriocin titer were done using procedures described by Gonzalez and Kunka (Gonzalez, C. F., and B. S. Kunka, Appl. Environ. Microbiol. 53:2534–2538 (1987)).

Plasmid isolation, electrophoresis and curing. Plasmid contents of the cultures were examined using the procedure described by Gonzalez and Kunka (Gonzalez, C. F. and B. S. Kunka, Appl. Environ. Microbiol. 46:81–89 (1983)).

Plasmid curing. Plasmid curing was done using high temperature and curing agents according to previously described procedures (Gonzalez, C. F., and B. S. Kunka, Appl. Environ. Microbiol. 46:81–89 (1983)).

Large scale culturing and processing for purification of bacteriocin(s). Four liters of MRS broth (Difco, Detroit, Mich.) was inoculated at 1% with an 8 hour old culture of strain NRRL-B-18809 grown in MRS broth and was grown statically at 32° C. for 24 hours. Cells were removed by centrifugation at 16,300 x g for 15 minutes at 4° C. The supernatant was filtered using a Minitan tangential filtration apparatus (Millipore, Bedford, Mass.) equipped with a 0.2 $\mu$m pore size polyvinylidene difluoride (PVDF) membrane. Bacteriocin production was assayed as previously described. Medium pH was less than 5.0.

Purification of LL-2. Filtrate from tangential filtration was adjusted to pH 4.0 using 10% hydrochloric acid and then was concentrated approximately 2-fold using a spiral-wound cellulose-based ultrafiltration cartridge with a 1 ft$^2$ surface area and a 3000 dalton molecular weight cutoff (Amicon SlY3, Beverly, Mass.). Concentration was performed at 4° C. using a peristaltic pump (Cole-Parmer, Chicago, Ill.) to maintain a 20 lb/in$^2$ differential across the membrane.

A 1600 ml aliquot of concentrated supernatant was applied to a 10 cm × 20 cm column (1.57 liters) of DEAE-650M anion exchange resin (Toso-Haas, Philadelphia, Pa.) equilibrated with 0.1M sodium acetate buffer, pH 4.0 at a flow rate of 10 ml/min. Absorbance of the eluent at 280 nanometers was monitored and eluent was collected from the first increase from baseline absorbance until baseline absorbance was again reached. The eluent volume was 3150 ml and the activity was 1600 AU/ml.

Preconcentration and anion exchange chromatography are necessary to achieve maximal binding of the bacteriocin to a cation exchange resin.

The entire volume of eluent from anion exchange chromatography was applied to a 10 cm×35 cm column (2.75 liters) of CM-650M cation exchange resin (Toso-Haas, Philadelphia, Pa.) which had been equilibrated against 0.1M sodium acetate buffer, pH 4.0. Activity was eluted using the same buffer containing 1M sodium chloride at pH 4.0. Eluent was collected from the first increase in conductivity from baseline conductivity $$\left(0.159 \frac{\text{micro siemens}}{\text{cm}}\right).$$

Collection was terminated when absorbance at 280 nanometers returned to baseline absorbance. The eluent volume was 2000 ml and the activity was 1600 AU/ml.

The eluent from cation exchange chromatography was concentrated approximately 20-fold by ultrafiltration until 110 ml remained (Amicon S1Y3, Beverly, Mass.). Sodium chloride content was then reduced approximately 5-fold by adding 500 ml deionized water and then concentrating to 110 ml again. The cartridge was emptied and then washed with 50 ml deionized water. The concentrate was combined with the wash solution to obtain 150 ml bacteriocin with 25,600 AU/ml activity.

Volume of the bacteriocin concentrate was further reduced using vacuum centrifugation (Savant, Farmingdale, N.Y.) until 12 ml remained. Aliquots of this concentrate were applied to a 2.5 cm×25 cm ODS column (Vydac, Hisperia, Calif.) equilibrated with 0.1% trifluoroacetic acid (TFA) in water. Activity was eluted using a gradient which typically used a linear change over 30 minutes to 45% acetonitrile containing 0.1% trifluoroacetic acid. A flow rate of 10 ml/min was used. Fractions were collected at 0.5 minute intervals and activity was located in the chromatogram by directly spotting 5 μl from each fraction onto an *P. pentosaceus* FBB 63C indicator plate. Protein elution was monitored using a UV detector (Beckman 166, San Ramon, Calif.) at 230 nanometers wavelength.

Two zones of activity were consistently observed, the first eluted at 27.5-28.5 minutes and the second eluted at 32-37 minutes. All fractions were dried using vacuum centrifugation, active fractions were reconstituted in 0.1 ml deionized water and were combined as follows. Active fractions eluting between 27.5 and 28.5 minutes were combined as LL-2A and active fractions eluting between 32.5 and 33 minutes were combined as LL-2B.

The LL-2A component was further purified by applying to a 2.5 cm×25 cm ODS column (Vydac, Hisperia, Calif.) as before. A gradient beginning at 20% and linearly progressing to 40% acetonitrile containing 0.1% TFA was performed over a 30 minute time frame. Activity was observed to elute between 26.5 and 28.0 minutes. Fractions within these elution limits were dried by vacuum centrifugation and then were combined as purified LL-2A.

Analytical HPLC. Purified protein was characterized by the appearance of peaks in the HPLC chromatogram using a 0.45×25 cm ODS column (Vydac, Hisperia, Calif.) with the UV detector set to monitor absorbance at 230 nanometers. Elution profiles were obtained using a gradient from 0.1% TFA to 45% acetonitrile containing 0.1% TFA.

Amino Acid Analysis. Samples for hydrolysis were dried by vacuum dehydration, reconstituted in 0.1 ml 6N HCl (Pierce, Rockford, Ill.), dried again, and hydrolyzed in vacuo at 110° C. in 8 mm×60 mm hydrolysis tubes (Pierce, Rockford, Ill.) for 24 hours in a Reacti-Therm heating block (Pierce, Rockford, Ill.). PITC derivatives were made using the directions supplied with a Pico-Tag derivatization system (Waters, Milford, Mass.) and PTC derivatives were detected at 254 nm using the suggested Pico-Tag protocol except that the reversed-phase column was a 0.45 cm×250 cm $C_{18}$ column (Beckman, SunRamoin, Calif.) instead of the proprietary Pico-Tag column.

Enzymatic Reactions. Trypsin and chymotrypsin susceptibility of crude and purified bacteriocin was explored. Enzymes were obtained from Sigma (St. Louis, Mo.) and were stored lyophilized at −20° C. until use. Enzymatic reactions were done in a 0.1M ammonium bicarbonate buffer, pH 7.8, containing 0.1 mM calcium chloride (Deutcher, M. P., Meth. Enzymol. 182:611–612 (1990)). Susceptibility was defined as inability of the bacterocin to inhibit the growth of a lawn of indicator bacteria when applied to the surface of an agar plate containing the bacteria at a rate of 16 units activity in a volume of 5 μl.

Amino Acid Sequencing. Sequence information was obtained with a gas phase sequencer (Applied Biosystems, Foster City, Calif.) using protocols supplied by the manufacturer.

SDS Polyacrylamide Gel Electrophoresis. Gels were prepared at either a fixed acrylamide concentration of 12.5% or as a linear gradient from 10% to 25%. The crosslinking agent was piperizine diacrylamide (BioRad, Richmond, Calif.). Gels were stained with Coomassie Brilliant Blue G followed by silver staining (BioRad, Richmond, Calif.) or were unstained in order to perform an activity analysis by overlaying the gel with soft agar containing indicator *P. pentosaceus* FBB-63C cells (Bhunia, J. Ind. Micro. Biol. 2:319–322 (1987)). The unstained gels were calibrated with pre-stained standards (BioRad, Richmond, Calif.).

Isolation and Characterization of Bacteriocin-Producing Lactococci. During the course of screening, a colony showing good antibacterial activity was observed. The colony was streaked and an isolated colony was propagated, retested for inhibitory activity and was stocked. The culture was found to be Gram-positive cocci arranged in short chains and the cell-morphology was oval and characteristic of lactic streptococci. The culture coagulated milk and was positive for sucrose fermentation. The culture was identified as *Lactococcus lactis* subsp. *lactis* and was designated as NRRL-B-18809.

The culture had a single, large plasmid pSRQ 400 (69 Kb in size). Curing of the plasmid employing high temperature incubation (42°–43° C.) resulted in the loss of inhibitory activity and ability to ferment lactose. Several repeated trials employing curing agents (acriflavin, proflavin, novobiocin) failed to yield colonies unable to ferment sucrose. From these results it was concluded that bacteriocin-production (Bac+) and lactose-fermentation phenotype (Lac+) were coded on the same plasmid and that sucrose fermentation (Suc+) was chromosomally determined. Bacteriocin-negative (Bac−) and lactose negative (Lac−) derivatives, however were resistant (Bac$^r$) to the bacteriocin produced by the parent. Hence, Bac$^r$ (or immunity) was coded on the chromosome.

The results of the preliminary characterization of crude bacteriocin in the cell-free filtrates are summarized in Tables 1 through 6.

From Table 1, it is evident that the crude bacteriocin in cell-free filtrate is greater than 100,000 Da indicating aggregation of multiple protein molecules.

TABLE 1

MOLECULAR WEIGHT OF CRUDE BACTERIOCIN FROM CELL-FREE FILTRATE OF NRRL-B-18809[1]

| MEMBRANE MWCO | RETENTATE VOLUME (ml) | PERMEATE VOLUME (ml) | BACTERIOCIN AU/ML RETENTATE | PERMEATE |
|---|---|---|---|---|
| 2,000 | 20 | 38 | 800 | None |
| 10,000 | 20 | 34 | 800 | None |
| 30,000 | 17 | 45 | 800 | None |
| 100,000 | — | — | 1600 | None |

[1] When purified, the bacteriocin has a molecular weight of about 6,600.

For maximal production of bacteriocin, MRS broth fortified with 1% yeast extract and 7% whey containing 0.5% yeast extract were suitable as can be seen from Table 2. Maximum bacteriocin titer was obtained at 24° C. and 32° C.; at 37° C. incubation, the titer was lower.

TABLE 2

EFFECT OF DIFFERENT MEDIA AND NUTRITIVE SUPPLEMENTS ON CRUDE BACTERIOCIN TITER IN CELL-FREE FILTRATES OF NRRL-B-18809.

| MEDIUM | SUPPLEMENT | pH | TITER (AU/ml) |
|---|---|---|---|
| MRS | — | 4.7 | 800 |
| MRS | 1% yeast extract | 4.7 | 1600 |
| APT | — | 4.3 | 800 |
| Skim Milk | — | 4.7 | 200 |
| Peptonized Milk | — | 4.8 | 800 |
| 7% Whey[1] | — | 4.3 | 400 |
| 7% Whey[1] | 0.2% yeast extract | 4.0 | 800+ |
| 7% Whey[1] | 0.5% yeast extract | 4.0 | 1600 |
| 7% Whey[1] | 1.0% yeast extract | 4.2 | 1600 |

[1] Whey powder contained 10% maltodextrin

The crude bacteriocin was stable at pH 4.1 at all the temperature treatments used including autoclaving (121° C. for 15 min.) as shown in Table 3.

TABLE 3

EFFECT OF HEAT ON CRUDE BACTERIOCIN IN CELL-FREE FILTRATE (pH 4.1) of NRRL-B-18809.

| Temperature of heating (°C.) | Duration (min) | Titer (AU/ml) |
|---|---|---|
| Control (iced) | 60 | 1600 |
| 21 | 60 | 1600 |
| 37 | 60 | 1600 |
| 60 | 60 | 1600 |
| 100 | 10 | 1600 |
| 121 | 15 | 1600 |

The crude bacteriocin was stable at pH 2.0–3.0 and progressively lost its activity at higher pH values as shown in Table 4.

TABLE 4

THE STABILITY OF CRUDE BACTERIOCIN FROM CELL-FREE FILTRATE OF NRRL-B-18809 DIALYZED AGAINST BUFFERS WITH OIFFERENT pH

| pH | Titer AU/ml |
|---|---|
| 2 | 1600 |
| 3 | 1600 |
| 4 | 800 |
| 5 | 800 |
| 6 | 200 |
| 7 | 400 |
| 8 | 200 |
| 9 | 400 |
| 10 | 400 |
| 11 | 400 |

As can be seen from Table 5, the crude bacteriocin was active against a wide range of Gram-positive bacteria with the exception of *Listeria monocytogenes* and *Staphylococcus aureus*. It had no activity against *E. coli*, a Gram-negative species.

TABLE 5

SPECTRUM OF ANTIMICROBIAL ACTIVITY

| | Indicator | | | | |
|---|---|---|---|---|---|
| | LL2 Crude | Nisin Crude | LL2A Pure | LL2B Pure | Nisin Pure |
| | | | Titer AU/ml | | |
| Indicator Strain | 1600 | 1600 | 3200 | 3200 | 3200 |
| L. plantarum 346 | + | + | + | + | + |
| L. plantarum 355 | + | + | — | + | + |
| L. casei 326 | + | + | — | + | + |
| L. casei 842 | + | + | — | + | + |
| L. brevis 329 | + | + | — | + | + |
| L. brevis 888 | + | + | + | + | + |
| L. fermentum 342 | + | + | — | + | + |
| L. fermentum 701 | + | + | + | + | + |
| P. acidilactici PAC 1.0 | + | + | — | + | + |
| P. acidilactici A | + | + | — | + | + |
| P. acidilactici B | + | + | + | + | + |
| P. acidilactici C | — | + | + | — | + |
| P. acidilactici D | — | + | + | — | + |
| P. pentosaceus FBB63C | + | + | + | + | + |
| L. monocytogenes 04 | — | — | + | + | + |
| L. monocytogenes 08 | — | — | + | + | + |
| L. monocytogenes 36 | — | — | + | + | + |
| L. monocytogenes 38 | — | — | + | + | + |
| L. monocytogenes 59 | — | — | + | + | + |
| L. monocytogenes 62 | — | — | + | + | + |
| L. monocytogenes 69 | — | + | + | + | + |
| S. mutans GS5 | + | — | — | + | + |
| S. mutans V262 | — | — | — | — | — |
| B. subtilis RM125 | + | ND | + | + | + |
| B. subtilis amylase+ | + | ND | — | + | + |
| L. lactis LLA 1.0 | — | — | — | + | + |
| L. lactis LLA 2.0 | — | + | — | + | + |
| L. lactis 367 | + | ND | ND | ND | ND |
| L. bulgaricus (4 strains) | + | ND | ND | ND | ND |
| S. aureus Z-88 | — | ND | | | |

TABLE 5-continued

SPECTRUM OF ANTIMICROBIAL ACTIVITY

| | Indicator | | | | |
|---|---|---|---|---|---|
| | LL2 Crude | Nisin Crude | LL2A Pure | LL2B Pure | Nisin Pure |
| | | | Titer AU/ml | | |
| Indicator Strain | 1600 | 1600 | 3200 | 3200 | 3200 |
| E. coli HB101 | — | ND | | | |

ND = not determined; + = inhibition; — = no inhibition

As can be seen from Table 6, the crude bacteriocin was resistant to treatment with 5% trypsin and alpha-chymotrypsin. Trypsin and chymotrypsin sensitivities of purified LL-2 bacteriocins to purified nisin were compared. Compared to nisin, LL-2 is more sensitive to chymotrypsin and more resistant to trypsin.

TABLE 6

EFFECT OF TREATMENT WITH TRYPSIN AND ALPHA-CHYMOTRYPSIN ON ANTIBACTERIAL ACTIVITY OF PURIFIED NRRL-B-18809 BACTERIOCIN

| TREATMENT | LL-2 Titer | Nisin Titer |
|---|---|---|
| Chymotrypsin 1 mg/ml | <200 (S) | >200 (R) |
| 100 µg/ml | <200 ↑ | >200 ↑ |
| 10 µg/ml | <200 ↓ | >200 ↓ |
| 1 µg/ml | <200 (S) | >200 (R) |
| Trypsin 1 mg/ml | >200 (R) | <200 (S) |
| 100 µg/ml | >200 ↑ | <200 ↑ |
| 10 µg/ml | >200 ↑ | <200 ↑ |
| 1 µg/ml | >200 ↑ | <200 ↓ |
| 100 ng/ml | >200 ↓ | <200 ↓ |
| 10 ng/ml | >200 ↓ | <200 (S) |
| 1 ng/ml | >200 (R) | >200 (R) |

Titer <200 is deemed sensitive to protease action; titer >200 is resistant.

Chymotrypsin digestion was done by 2 hour incubation at 40° C. with 3200–6400 AU/ml bacteriocin concentration.

Trypsin digestion was done by 20 hour incubation at 40° C. 3200–6400 AU/ml bacteriocin concentration.

The use of purified bacteriocin in enzyme sensitivity testing is preferred since the crude media can contain an unknown protease inhibition activity or other phenomena which would tend to confound results.

As shown by Table 7, purified LL-2 was obtained in good yield and high purity.

TABLE 7

PURIFICATION OF BACTERIOCIN LL-2

| Step | Units Activity AU/ml | Specific Activity AU/mg protein | Yield Percent % | Fold Purification |
|---|---|---|---|---|
| Filtered Supernatant | $6.4-10^6$ | 74 | 100 | |
| Ultrafiltration | $5.1-10^6$ | 139 | 80 | 2 |
| Anion Exchange | $5.0-10^6$ | 319 | 79 | 4 |
| Cation Exchange | $3.2-10^6$ | 1702 | 50 | 23 |
| Diafiltration | $3.8-10^6$ | 6259 | 60 | 85 |
| Concentration | $3.1-10^6$ | nd | 48 | nd |
| HPLC | | | | |
| LL-2A | $1.8-10^4$ | $7.5-10^3$ | 0.3 | 101 |
| LL-2B | $1.6-10^6$ | $7.0-10^5$ | 25 | 9500 |

Figure 2:
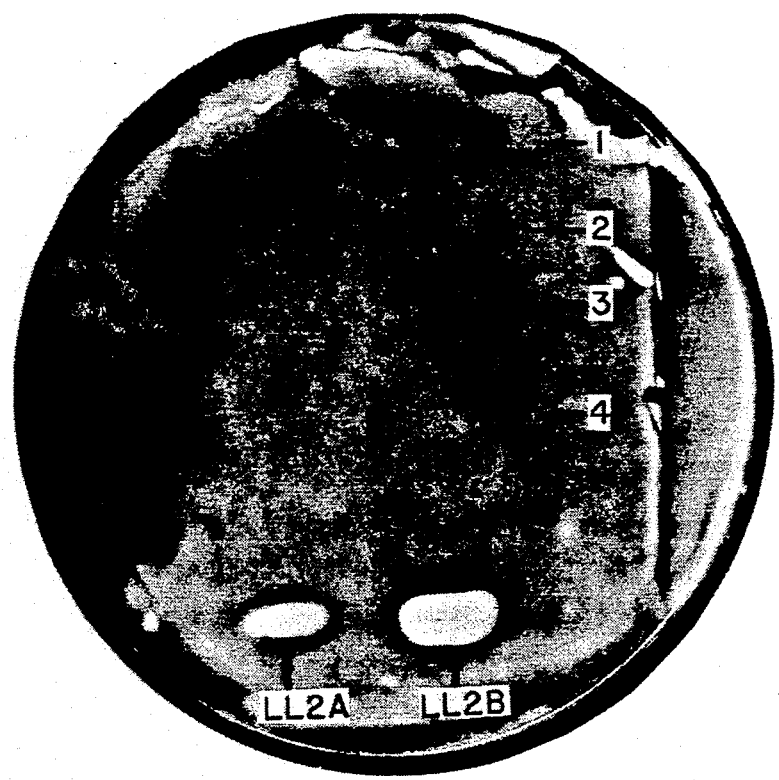
FIG. 2 shows inhibition zones produced on overlay gels with HPLC purified bacteriocins LL-2A and LL-2B, using a sensitive *Pediococcus pentosaceus* FBB63C as an indicator strain.

The LL-2B component as shown in Table 7 accounted for more than 90% of the activity. 25% of the activity initially present was recovered. The two bacteriocins LLB-2A and LLB-2B obtained as a result of HPLC purification were active on overlay gels with activity centered about a region corresponding to molecular weight 6500 daltons as shown by FIG. 2.

Analytical HPLC results show that LL-2A and LL-2B are related. Purified LL-2B will produce LL-2A over time, although purified LL-2A does not produce LL2-B. Nisin is also known to consist of several molecular species in addition to the parent protein. The most predominant is the parent structure lacking two carboxy terminal residues and containing a terminal Val-$NH_2$. These results are consistent with the hypothesis that LL-2A is a product of degradation of LL-2B and that this degradation product is formed in a similar manner to that of the nisin degradation product. The degradation product of nisin however was reported inactive as a bacteriocin, whereas LL-2A retains a wide spectrum of bacteriocin activity.

Figure 1B:
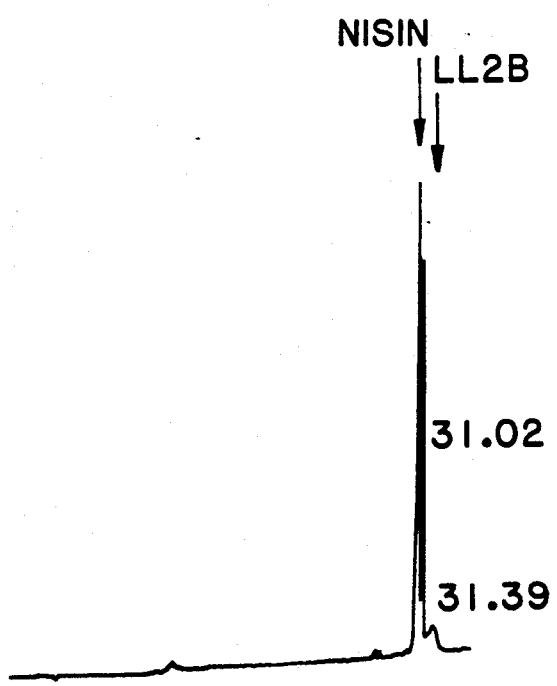

Analytical HPLC results of the mixture of LL-2A, LL-2B and nisin illustrate that molecular differences are present between the molecules. These differences provide a small but significant difference in HPLC elution time which is readily apparent in chromatograms of mixtures of LL-2A, LL-2B and nisin as shown in FIGS. 1A and 1B. The elution of LL-2B before nisin shows a more hydrophilic nature of LL-2B compared to nisin.

EXAMPLE 2

A DNA sequence was found in NRRL-B-18809 cells which produced a polypeptide corresponding to the sequence of nisin except that $His_{27}$ is replaced by $Asn_{27}$ resulting from a change from CAT to AAT in the DNA. Amino acid composition results shown in Table 8 confirm the loss of one His residue from the amino acid make-up of LL-2B. Results from amino acid sequencing of LL-2B indicate an amino terminal isoleucine residue is followed by no other residues presumably due to an N-terminal blockage at the second residue. This result is also found for nisin, since the second residue, a dehydrobutyrine residue, has been found to cyclize after Edman degradation of the previous residue thus blocking further sequencing.

The following data shows how the results were obtained.

TABLE 8

AMINO ACID COMPOSITION OF LL-2B COMPARED TO NISIN

| | LL-2B | Theo. LL-2 | Nisin | Theo. Nisin |
|---|---|---|---|---|
| D Asp/Asn | 1.4 | 2 | 0.5 | 1 |
| E Glu/Gln | 0.8 | 0 | 0.0 | 0 |
| S Ser | 1.0 | 1 | 0.8 | 1 |
| G Gly | 2.7 | 3 | 3.4 | 3 |
| H His | 0.8 | 1 | 2.4 | 2 |
| R Arg | 0.0 | 0 | 0.0 | 0 |
| R Thr | 0.0 | 0 | 0.0 | 0 |
| A Ala | 1.8 | 2 | 1.8 | 2 |
| P Pro | 1.0 | 1 | 1.2 | 1 |
| Y Tyr | 0.0 | 0 | 0.0 | 0 |
| V Val | 1.4 | 1 | 1.3 | 1 |
| M Met | 0.6 | 2 | 1.2 | 2 |
| C Cys | 0.0 | 0 | 0.0 | 0 |
| I Ile | 4.7 | 3 | 3.1 | 3 |
| L Leu | 1.9 | 2 | 2.1 | 2 |
| F Phe | 0.0 | 0 | 0.0 | 0 |
| K Lys | 2.8 | 3 | 3.2 | 3 |
| | 21.0 | 21.0 | 21.0 | 21.0 |

Total DNA isolation. Total genomic DNA from *Lactococcus lactis* NRRL-B-18809 was isolated according to methods described elsewhere (van der Vossen, J.

M. B. M., van der Lelie, D., and Venema, G., Appl. Environ. Microbiol. 53:2452-2457 (1987)).

Polymerase Chain Reaction (PCR). Deoxy-oligonucleotide PCR primers were based on the nucleotide sequence flanking the structural gene for the precursor of the bacteriocin nisin produced by *Lactococcus lactis* F15876 (Dodd, H. M., Horn, N., and Gasson, M. J., J. Gen. Microbiol. 136:555-566 (1990)). The two primers were synthesized on a DNA-synthesizer (Applied Biosystems 380A, Foster City, Calif.) using the Phosphoamidit technique (Barone, A. D., et al., Nucleic Acid Research, 12:4051-4061 (1984)). The 20-base primer Ns-A (5'-CGCGAGCATAATAAACGGCT-3', sense primer) starts 100 bases upstream of the ATG start codon, while the 21-base primer Ns-B (5'-GGATAG-TATCCATGTCTGAAC-3', antisense primer) starts 47 bases downstream of the TAA stop codon.

AmpliTaq- Recombinant Taq DNA polymerase (Perkin-Elmer/Cetus Corp., Norwalk, Conn.) was used to carry out the PCR using a Perkin Elmer Cetus DNA Thermal Cycler (Perkin-Elmer/Cetus Corp., Norwalk, Conn.). The manufacturer's recommendations were followed with slight modifications. Each 100-μl reaction mixture included 100 pmol of each primer and approximately 10 ng of template DNA. To minimize the synthesis of regions caused by low-stringency annealing of primers the reaction mixtures were incubated at 94° C. for 5 minutes before cycle 1. Each of the 30 cycles consisted of 1 minute at 94° C., 1.5 minute at 55° C., and 2 minutes at 72° C. After the last cycle the polymerization step was extended by 5 minutes at 72° C. to complete synthesis of all strands.

Electrophoresis. PCR products (10-μl portions) were analyzed by electrophoresis on 1.5% agarose gels in Tris-borate-EDTA buffer (Maniatis, T., Fritsch, E. F., and Sambrook, J., Molecular Cloning: A Laboratory Manual. Cold Spring Harbor, N.Y., (1982)).

Sequence Analysis. Prior to sequencing PCR products were purified via an electro-elution step (Maniatis, T., Fritsch, E. F., and Sambrook, J., Molecular Cloning: A Laboratory Manual. Cold Spring Harbor, N.Y., (1982)). PCR products were sequenced by the dideoxy chain termination procedure (Sanger, F., Nicklen, S., and Coulson, A. R., Proc. Natl. Acad. Sci. U.S.A., 74:5463-5467 (1977)), using the Sequenase 2.0 kit (U.S. Biochemicals, Cleveland, Ohio) with the following modifications. The heat-denaturation step (3 minutes at 95° C.) was directly followed by a short annealing phase at −70° C. The labelling reaction mixture was incubated at 37° C. for 30 to 45 seconds. The sequencing reaction products were separated on a denaturing polyacrylamide gel with a buffer gradient as described by Biggin et al., (Biggin, M. D., et al., Proc. Natl. Acad. Sci. U.S.A., 80:3963-3965 (1983)).

Determination of the nucleotide sequence of a gene encoding a bacteriocin precursor from Lactococcus lactis NRRL-B-18809. To determine whether bacteriocin LL-2 had homology with nisin, a bacteriocin which is produced by several other *Lactococcus lactis* strains (Dodd, H. M., Horn, N., and Gasson, M. J., J. Gen Microbiol. 136:555-566 (1990)), a PCR (Polymerase Chain Reaction) analysis on total DNA from *Lactococcus lactis* NRRL-B-18809 was performed. Two nisin-specific primers (Ns-A and Ns-B) based on the nucleotide sequence surrounding the gene for the precursor of nisin (Dodd, H. M., Horn, N. and Gasson, M. J., J. Gen. Microbiol. 136:555-566 (1990)) were synthesized and used in the PCR using a total DNA preparation of *Lactococcus lactis* NRRL-B-18809 as template. The PCR generated a molecule which had the predicted size (i.e. 321 bp), as determined by agarose gel electrophoresis. The molecule was similar in size to a DNA molecule that was generated on total genomic DNA of a *Lactococcus lactis* strain NRRL-B-18535 as described in Ser. No. 07/492,969 using the same primers. Controls, which lacked either primers or template DNA, yielded no DNA molecules. Sequencing of the PCR-generated molecule from *Lactococcus lactis* NRRL-B-18809, using both Ns-A and Ns-B as sequencing primers resulted in nucleotide sequence similar to the sequence of the gene encoding precursor nisin and its flanking regions (Dodd, H. M., Horn, N., and Gasson, M. J., J. Gen. Microbiol. 136:555-566 (1990)), except for one base difference within the structural gene. At position 2362 (map position of *Lactococcus lactis* F15876 (Dodd, H. M., Horn, N., and Gasson, M. J., J. Gen. Microbiol. 136:555-566 (1990)) an adenosine (A) was present instead of a cytosine (C) at the corresponding position in the gene for precursor polypeptide (SEQ ID NO: 1). The nucleotide sequence of the corresponding region in the NRRL-B-18535 PCR-generated molecule did not show the alteration. Due to the alteration in the genomic DNA of NRRL-B-18809, the amino acid, asparagine (Asn) is predicted at position 27 of mature bacteriocin. In nisin, instead, histidine (His) is encoded at this position. This indicates that bacteriocin LL-2 is similar to, but not identical to nisin. These results confirm the data on the amino acid composition of bacteriocin LL-2 in which the ratio of asparagine:histidine is 2:1, rather than 1:2 in mature nisin as shown in FIG. 8.

Table 9 shows the amino acids for the Xaa residues shown in SEQ ID No: 2. There are a limited number of possibilities for Xaa. (Cys is Xac; Ser is Xaa and Thr is Xab except as written in SEQ ID NO:2)

TABLE 9

| Translated Amino Acid | Sequence Position | Final form of amino acid |
|---|---|---|
| Cys | 7,11,19,26,28 | Ala—S— |
| Ser | 3,5,29,33 | Ala or Dha or Ser |
| Thr | 2,8,13,23,25 | Abu or Dhb |

As can be seen in Table 9, the Xaa at each sequence position SEQ ID NO:2 represents one of only two or three choices based on the types of post-translational modification presumed to occur in this cell line. Amino acid analysis shows no cysteine, no threonine and a single serine residue. Amino acid analysis of nisin is identical for these three residue types. Xaa arising from Cys and Thr represent one of only two possibilities, since the unmodified amino acid is not a possibility in LL-2.

The polypeptide has a tentative formula

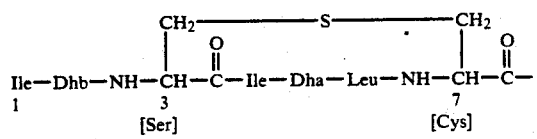

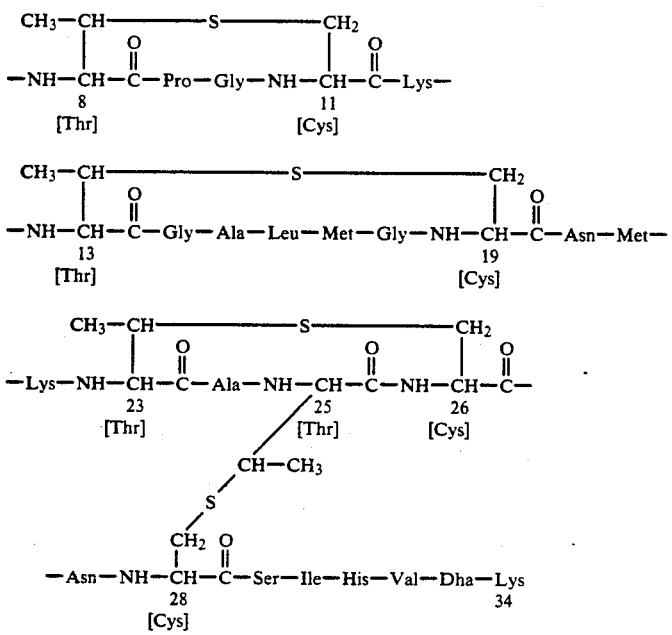

wherein Dha is 2-aminopropenoic acid, Dhb is 2-aminobut-2-enoic acid, and the amino acid names between brackets below the partial chemical formulae indicate the original amino acids from which these atypical amino acid residues were formed. The sequences are shown in SEQ ID NO.:2 with Xaa as discussed previously.

EXAMPLE 3

Effect of adding different levels of the crude LL-2 bacteriocin of Example 1 lyophilized to a powder on post-acidification (spoilage) of yogurt held at 12C:

Yogurt was made by inoculating sterile 11% reconstituted non-fat dried milk with a yogurt starter culture and incubating at 35° C. for 16 hr. At the end of incubation, the yogurt was chilled in an ice-bath. After homogeneous mixing, 100 gm. portions were transferred into five wide-mouth screw-cap bottles which were labelled 0 (Control), 2%, 3%, 4%, and 5%. Nothing was added to the bottle marked 0. Crude lyophilized LL-2 bacteriocin powder (containing bacteriocin titer of 8000 AU/gm.) was added in the amounts of 2 gm., 3 gm., 4 gm., and 5 gm. to bottles labelled 2%, 3%, 4% and 5%, respectively. After uniform mixing of the powder, the yogurt pH was measured and the bottles were placed in an incubator adjusted to hold at 12° C. After 6 and 13 days, the pH values of the individual bottles were measured and recorded. The results were plotted and are shown in FIG. 3.

It is intended that the foregoing description be only illustrative of the present invention and that the present invention be limited only by the hereinafter appended claims.

---

We claim:

1. An isolated and purified polypeptide having an inhibitory activity against sensitive Gram-positive bacteria and obtained from a polypeptide precursor consisting essentially of amino acids 1 to 34 of SEQ ID NO:1.

2. An isolated and purified polypeptide having an inhibitor activity against sensitive Gram-positive bacteria and having the amino acid sequence consisting essentially of Ile Xab Xaa Ile Xaa Leu Xac Xab Pro Gly Xac Lys Xab Gly Ala Leu Met Gly Xac Asn Met Lys Xab Ala Xab Xac Asn Xac Xaa Ile His Val Xaa Lys wherein Xaa is selected from Ser, Ala-, or Dha, and Xab is selected from Abu-, or Dhb, and Xac is selected from Ala-S-, where Ala- is 3-substituted Alanine (—(CO)CH(NH—)CH₂—), Abu- is 3-substituted 2-aminobutanoic acid (—(CO)CH(NH—)CH(CH₃)—), Ala-S- is (3-alanyl)-thio, Abu is 2-amino butanoic acid, Dha is 2-amino propenoic acid and Dhb is 2-aminobut-2-enoic acid, and subunits thereof having an essentially equivalent inhibitor activity to the sensitive bacteria and wherein there are sulfur bridges between the amino acids which provide the activity wherein the polypeptide is derived from a precursor polypeptide containing amino acids 1 to 34 of SEQ ID NO: 1.

3. An isolated and purified polypeptide of claim 2 as produced by *Lactococcus lactis* subspecies lactis NRRL-B-18809 in a growth medium and having inhibitory activity against sensitive Gram-positive bacteria.

4. The polypeptide of claim 3 wherein the polypeptide has been purified by ultrafiltration and wherein the polypeptide is a retentate in the ultrafiltration.

5. The polypeptide of claim 3 wherein the polypeptide has been purified chromatographically using an anion exchange resin.

6. The polypeptide of claim 5 wherein in addition the polypeptide has been purified by ultrafiltration.

7. The polypeptide of claim 3 or a product containing the polypeptide in freeze dried form.

8. An isolated and purified polypeptide precursor consisting essentially of amino acids 1 to 34 of SEQ ID NO:1.

9. An isolated and purified polypeptide precursor having the sequence consisting essentially of amino acids -23 to 34 of SEQ ID NO:1.

* * * * *

UNITED STATES PATENT AND TRADEMARK OFFICE
CERTIFICATE OF CORRECTION

PATENT NO. : 5,231,165

DATED : July 27, 1993

INVENTOR(S) : Ebenezer R. Vedamuthu, James T. Henderson, John D. Marugg and Pieter D. VanWassenaar It is certified that error appears in the above-indentified patent and that said Letters Patent is hereby corrected as shown below:

TITLE PAGE:

In the Abstract, a period --.-- should be inserted after "described" and before "Methods".

Column 1, line 7, "5,173,277" should be --5,173,297--.

Column 5, line 20, "HLC" should be --HPLC--.

Column 9, line 65, Table 4, "oifferent" should be --different--.

Column 10, line 45, "L. brevis 329 + + - + +" should read -- L. brevis 329 + + + + +--.

Column 10, line 46, "L. brevis 888 + + + + +" should read -- L. brevis 888 + + - + +--.

Column 11, line 54, "6.4 - 106" should be --$6.4 - 10^6$--.

Column 12, line 6, "LL2-B" should be --LL-2B--.

UNITED STATES PATENT AND TRADEMARK OFFICE
CERTIFICATE OF CORRECTION

PATENT NO. : 5,231,165
DATED : July 27, 1993
INVENTOR(S) : Ebenezer R. Vedamuthu, James T. Henderson, John D. Marugg and Pieter D. VanWassenaar It is certified that error appears in the above-indentified patent and that said Letters Patent is hereby corrected as shown below:

Column 12, (Table 8) line 53, "H His 0.8 1 24 2" should read -- H His 0.8 1 2.4 2 --.

Column 17 (Claim 2) line 50, "inhibitor" should be --inhibitory--.

Column 17 (Claim 2) line 66, "inhibitor" should be --inhibitory--.

Signed and Sealed this

Twenty-ninth Day of March, 1994

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 321 base pairs
        ( B ) TYPE: Nucleic Acid
        ( C ) STRANDEDNESS: Double
        ( D ) TOPOLOGY: Linear ( i i ) MOLECULE TYPE: Other DNA ( i i i ) HYPOTHETICAL: No ( i v ) ANTI-SENSE: No ( v i ) ORIGINAL SOURCE:
        ( A ) ORGANISM: Lactococcus lactis subspecies lactis
        ( B ) STRAIN: NRRL-B-18809
        ( C ) INDIVIDUAL ISOLATE: LLA-2.0
        ( G ) CELL TYPE: Unicellular organism -continued ( i x ) FEATURE:
    ( A ) NAME/KEY: bacteriocin encoding DNA
    ( B ) LOCATION: 101 to 271
    ( C ) IDENTIFICATION METHOD: sequencing ( x i ) SEQUENCE DESCRIPTION: SEQ ID NO:1:

```
CGCGAGCATA ATAAACGGCT CTGATTAAAT TCTGAAGTTT GTTAGATACA ATGATTTCGT    60

TCGAAGGAAC TACAAAATAA ATTATAAGGA GGCACTCAAA ATG AGT ACA AAA GAT     115
                                              Met Ser Thr Lys Asp
                                                          -20

TTT AAC TTG GAT TTG GTA TCT GTT TCG AAG AAA GAT TCA GGT GCA TCA     163
Phe Asn Leu Asp Leu Val Ser Val Ser Lys Lys Asp Ser Gly Ala Ser
            -15             -10                 -5

CCA CGC ATT ACA AGT ATT TCG CTA TGT ACA CCC GGT TGT AAA ACA GGA     211
Pro Arg Ile Thr Ser Ile Ser Leu Cys Thr Pro Gly Cys Lys Thr Gly
     1              5                       10

GCT CTG ATG GGT TGT AAC ATG AAA ACA GCA ACT TGT AAT TGT AGT ATT     259
Ala Leu Met Gly Cys Asn Met Lys Thr Ala Thr Cys Asn Cys Ser Ile
 15              20              25              30

CAC GTA AGC AAA TAACC AAATCAAAGG ATAGTATTTT GTTAGTTCAG ACATGGATAC   316
His Val Ser Lys

TATCC                                                                321
```

( 2 ) INFORMATION FOR SEQ ID NO:2:

( i ) SEQUENCE CHARACTERISTICS:
        ( A ) LENGTH: 34 Amino Acids
        ( B ) TYPE: Amino Acid
        ( D ) TOPOLOGY: Linear ( i i ) MOLECULE TYPE: Protein ( x i ) SEQUENCE DESCRIPTION: SEQ ID NO:2:

```
Ile Xaa Xaa Ile Xaa Leu Xaa Xaa Pro Gly Xaa Lys Xaa Gly Ala Leu
 1           5                    10              15

Met Gly Xaa Asn Met Lys Xaa Ala Xaa Xaa Asn Xaa Xaa Ile His Val
         20              25              30

Xaa Lys
```